United States Patent [19]

Uram

[11] Patent Number: 5,213,092
[45] Date of Patent: May 25, 1993

[54] ASPIRATING ENDOSCOPE

[76] Inventor: Martin Uram, 39 Sycamore Ave., Little Silver, N.J. 07739

[21] Appl. No.: 785,996

[22] Filed: Oct. 31, 1991

[51] Int. Cl.5 .............................................. A61B 1/06
[52] U.S. Cl. ........................................ 128/4; 128/6; 128/4 A
[58] Field of Search .................. 606/4, 107, 162, 166; 128/4, 648, 745, 747, 6, 4 A, 7, 8, 9; 604/118, 22

[56] References Cited

U.S. PATENT DOCUMENTS

| | | | |
|---|---|---|---|
| 3,735,751 | 5/1973 | Katz | 128/750 |
| 3,913,568 | 10/1975 | Carpenter | 128/11 |
| 3,941,121 | 3/1976 | Olinger et al. | 128/6 |
| 4,607,622 | 8/1986 | Fritch et al. | 606/4 X |
| 4,922,902 | 5/1990 | Wuchinich et al. | 606/168 X |
| 4,998,527 | 3/1991 | Meyer | 128/6 |
| 5,112,328 | 5/1992 | Taboada et al. | 128/898 X |

Primary Examiner—Richard J. Apley
Assistant Examiner—Karen Ann Jalbert
Attorney, Agent, or Firm—McAulay Fisher Nissen Goldberg & Kiel

[57] ABSTRACT

A surgical and operating endoscope adapted for use in ophthalmological surgery has an intraocular probe. The probe has first and second cylindrical portions. The first portion contains an image guide composed of a large number of optical fiber elements. The image guide is surrounded by an annulus of illuminating optical fiber elements. Adjacent to and parallel to the imaging and illuminating portion is the second cylindrical portion which is an aspirating cannula. The distal end of the aspirating cannula extends distally two millimeters past the distal end of the imaging and illuminating portion in order to hold tissue that is being pulled toward the aspirating port away from the image plane of the image guide.

8 Claims, 1 Drawing Sheet

ASPIRATING ENDOSCOPE

BACKGROUND OF THE INVENTION

This invention relates in general to an aspirating endoscope and more particularly to one that is adapted to be used in various ophthalmological procedures.

In general terms, a large number of different types of endoscopes are known and used in the medical field.

In ophthalmology, it is usual to use an irrigating and aspirating surgical instrument which is positioned by the use of an operating microscope. But there are eye locations which the operating microscope cannot image and there are eye conditions which limit the field of the operating microscope.

In ophthalmology, the problems include the aspiration of lens material that is lodged behind the iris and cannot be viewed during cataract extraction. Problems also arise in eyes that cannot achieve wide pupillary dilation which occurs, for example, in various forms of glaucoma, uveitis (inflammation) and pediatric cataract and especially those pediatric cataracts that are associated with congenital ocular anomalies. These types of circumstances make it difficult to completely remove the cataractous lens material and therefore increases the potential for post operative complications.

Accordingly, an important purpose of this invention is to provide an aspirating endoscope that is particularly adapted for ophthalmological use in areas that cannot be normally viewed.

BRIEF DESCRIPTION

A surgical endoscope adapted for use in portions of the eye which cannot be imaged by an operating microscope has a hand piece to which there is attached a distally extending intraocular probe. The intraocular probe contains a first tubular portion that provides both illuminating light and imaging. Welded to this first portion is a second tubular portion which provides aspiration. These two tubular portions have axes that are parallel to one another and are welded to one another along an axially extending seam.

The imaging and illuminating portion has a central core composed of a large number of optical fiber elements to provide an image of the tissue being viewed. The tissue being viewed is illuminated by light provided through illuminating optical fibers arranged in an annulus around the imaging core. A lens having a depth of field that extends down to one mm is bonded to the distal end of this first portion.

The second portion is the aspirating cannula. It has an open end port. It extends approximately two mm distally of the end of the imaging and illuminating portion. In this fashion, tissue held against the open distal end of the aspirating cannula can be viewed by the surgeon even if the tissue bulges proximally by a distance of up to one millimeter.

DESCRIPTION OF THE PREFERRED EMBODIMENTS

As shown in the FIGs, one embodiment of the endoscope of this invention has a hand piece 10, an intraocular probe 12 and a flexible cable 14 that connects the proximal end of the hand piece 10 to a connector 16. From the connector 16, coupling is made to respectively: a vacuum (not shown), an eyepiece or other image receiving media (also not shown) and a source of illumination (also not shown).

Figure 1:
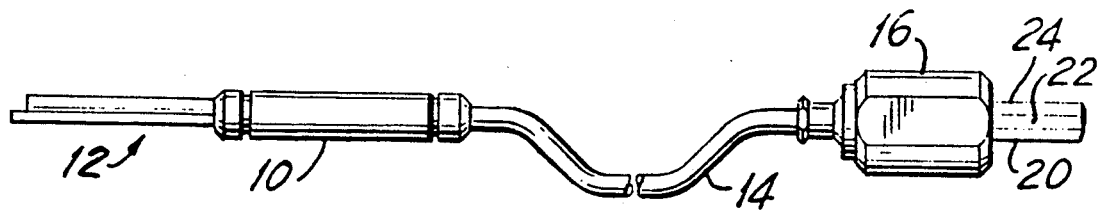
FIG. 1 is a side view of an embodiment of this invention in which the intraocular portion that is of primary significance to this invention is shown on the left.
Figure 2:
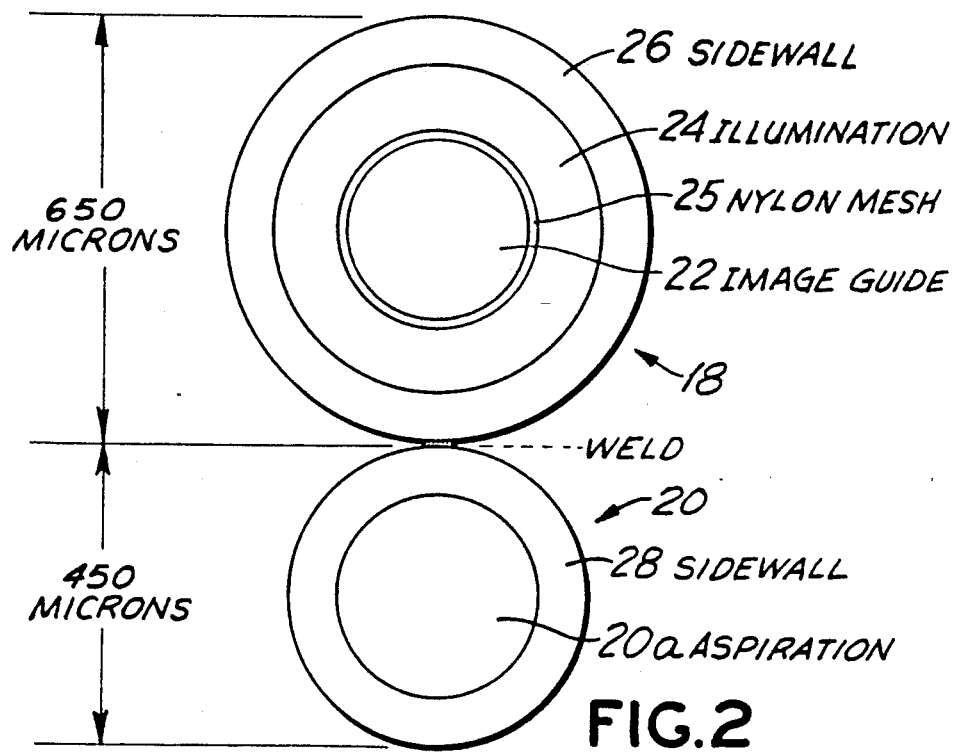
FIG. 2 is an end view of the intraocular portion of FIG. 1 illustrating the imaging/illuminating guide on top and the aspirating cannula on the bottom.

Within the cable 14, hand piece 10 and intraocular probe portion 12, there are deployed three separate elements that perform three separate functions. The deployment of these three separate elements within the probe 12, is shown in the cross-sectional view of FIG. 2. The probe 12 has an imaging and illumination portion 18 and an aspirating portion 20.

A central zone of the portion 18 performs an imaging function. This image guide 22, in one embodiment, has approximately 3,000 optical fibers, each optical fiber having approximately a three micron diameter to thereby provide a 3,000 pixel image. The diameter of this image guide 22 is about 300 microns (0.3 mm). In an annular zone surrounding the image guide 22 there is an illumination zone 24. This illumination zone is composed of a large number of three micron fibers which carry illumination toward the distal end of the probe 12. The annulus 24 has a thickness of about 100 microns (0.1 mm) A twenty-five micron nylon mesh layer 25 is a boundary layer between the image guide 22 and illumination zone 24. The portion 18 is enclosed in a stainless steel tube 26 having an outer diameter of 650 microns and a wall thickness of 75 microns.

In operation, light is transmitted down the illumination zone 24 to emerge at the distal end of the probe 12 and provide illumination at the area of operation. The image of at least part of the area illuminated is transmitted back through the image guide 22 to be viewed by the surgeon at an eyepiece (not shown).

The aspirating portion 20 is a separate cylindrical element welded to the surface of the tube 26. This aspirating portion 20 has a stainless steel tubular sidewall 28 with a outside diameter of 450 microns and a wall thickness of 75 microns to provide a 300 micron aspirating port 20w. The distal end 20a of the tube 20 is open to provide the aspirating port through which tissue is aspirating out the cannula 20.

Figure 3:
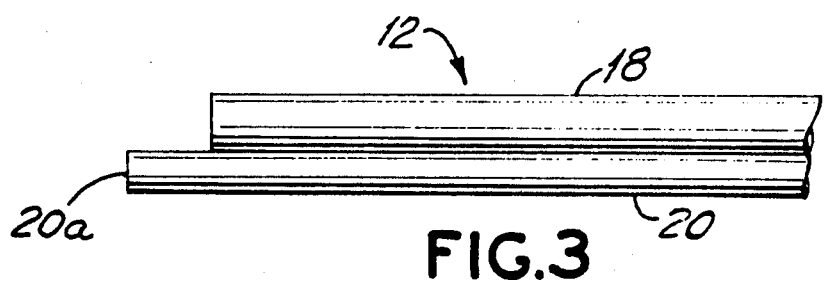
FIG. 3 is a side view of the distal end of the intraocular portion on a much larger scale than is shown in FIG. 1 in order to illustrate the two millimeter set back of the distal end of the imaging and illuminating guide from the distal end of the aspirating cannula.

Most importantly, as shown in FIG. 3, the imaging and illumination portion 18 has a distal end which is set back from the distal end of the aspiration portion 20 by two millimeters.

In one preferred embodiment, an objective lens is bonded to the distal end of the imaging and illuminating portion 18 and provides a depth of field from one mm to infinity with a field of view of 70 degrees. A depth of field down to as little as one mm is important to aid the surgeon to position the distal end of the probe adjacent to the tissue which is to be aspirated. However, the aspirating cannula 20 extends two millimeters beyond the distal end of the image guide 22 in order to avoid having tissue block the surgeon's view. It is important that a clear view be maintained during the controlled aspiration of lens material.

Tissue which is held at the aspirating port may bulge proximally around the aspirating distal end but not by enough to cover and block the distal end of the image guide 22. Essentially the end of the aspirating cannula 20 holds tissue away from the one mm limit to the viewing field of the image guide.

The lens is a triple lens of a known type. It is bonded to the image guide 22 prior to welding the tubes 26 and 28.

At the juncture 16, the imaging set of optical fibers 20 is separated from the illumination set 24 to be appropriately connected to an eye piece for the imaging set 20 and to a source of light for the set of fibers that constitute the illumination zone 24.

It should be noted that the image provided by the image guide 20 can be applied to an eye piece or can be displayed by a video or can be applied to create a still photograph. Indeed, it is anticipated that a video display might be preferable to facilitate the surgeon's positioning in order to manipulate the probe 12 properly.

In one embodiment, the intraocular probe is 33 mm long to the aspirating port 20a, the handpiece is 40 mm long and the flexible cable is 1800 mm long.

It should be noted that a known type of plastic sleeve can be fit around the combined portions 18 and 20 and extended proximally to a source of saline to provide irrigation by a known technique.

In use this aspirating endoscope can be used in a number of different situations. It can be used to remove fragments of tissue that cannot be seen after a phaco emulsification process. It can be used in certain pediatric procedures to remove the entire, relatively soft, cataract.

What is claimed is:

1. An ophthalmological endoscopic probe extending distally from a hand piece, comprising:
   a longitudinally extending aspirating cannula having an open distal end and a first longitudinal axis, and
   a longitudinally extending illumination and imaging guide comprising:
   i. a tubular housing having a second longitudinal axis and a second distal end,
   ii. a first set of longitudinally extending optical fibers within said housing which act as an image guide for transmitting an image from an operation area to a viewing device, said fibers arranged in a cylindrical bundle, said bundle being centered on said second longitudinal axis and extending to said second distal end,
   iii. a second set of longitudinally extending optical fibers which act as an illumination guide for transmitting light from a light source to the operation area, said second set being arranged as an annulus around said first set within said housing and extending to said second distal end,
   said first and second sets of optical fibers being the sole elements within said tubular housing and having a cross-section substantially congruent with the inner cross-section of said housing,
   said aspirating cannula and said housing being fixed adjacent to one another with their respective longitudinal axes parallel to one another,
   said distal end of said aspirating cannula extending distally past said distal end of said housing.

2. The endoscope improvement of claim 1 further comprising:
   an objective lens bonded to the distal end of said image guide to provide a depth of field that extends down to approximately one mm.

3. The improved endoscope of claim 2 wherein:
   said illuminating and imaging guide has an image guide portion with approximately 3,000 optical fibers, each optical fiber having approximately a three micron diameter, to provide a 3,000 pixel image.

4. The endoscope improvement of claim 3 wherein said illuminating and imaging guide has an outer diameter of approximately 650 microns and said aspirating cannula has an outer diameter of approximately 450 microns.

5. The endoscope improvement of claim 2 wherein said illuminating and imaging guide has an outer diameter of approximately 600 microns and said aspirating cannula has an outer diameter of approximately 450 microns.

6. The improved endoscope of claim 1 wherein:
   said illuminating and imaging guide has an image guide portion with approximately 3,000 optical fibers, each optical fiber having approximately a three micron diameter, to provide a 3,000 pixel image.

7. The endoscope improvement of claim 6 wherein said illuminating and imaging guide has an outer diameter of approximately 650 microns and said aspirating cannula has an outer diameter of approximately 450 microns.

8. The endoscope improvement of claim 1 wherein said illuminating and imaging guide has an outer diameter of approximately 650 microns and said aspirating cannula has an outer diameter of approximately 450 microns.

* * * * *